(12) United States Patent
Dorati et al.

(10) Patent No.: US 9,170,131 B2
(45) Date of Patent: Oct. 27, 2015

(54) APPARATUS AND METHOD FOR DETECTING THE POSITION OF APPLICATION OF A SEALING STRIP ONTO A WEB OF PACKAGING MATERIAL FOR FOOD PRODUCTS

(75) Inventors: Alberto Dorati, Modena (IT); Roberto Ansaloni, Formigine (IT); Roberto Gramazio, Modena (IT)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 1225 days.

(21) Appl. No.: 13/125,149

(22) PCT Filed: Nov. 17, 2009

(86) PCT No.: PCT/EP2009/065341
§ 371 (c)(1),
(2), (4) Date: Apr. 20, 2011

(87) PCT Pub. No.: WO2010/057896
PCT Pub. Date: May 27, 2010

(65) Prior Publication Data
US 2011/0203221 A1    Aug. 25, 2011

(30) Foreign Application Priority Data

Nov. 18, 2008 (EP) .................................... 08169383

(51) Int. Cl.
*G01D 5/34* (2006.01)
*G01N 21/89* (2006.01)
(Continued)

(52) U.S. Cl.
CPC ............ *G01D 5/342* (2013.01); *B29C 65/4815* (2013.01); *B29C 65/5042* (2013.01);
(Continued)

(58) Field of Classification Search
None
See application file for complete search history.

(56) References Cited

U.S. PATENT DOCUMENTS 3,835,332 A * 9/1974 Bridges .................... 250/559.04
4,682,038 A * 7/1987 Focke .......................... 250/548
(Continued)

FOREIGN PATENT DOCUMENTS

DE    20 2005 007 089 U1    7/2005
DE    10 2004 040 345 A1    3/2006
(Continued)

OTHER PUBLICATIONS

Japanese Office Action dated Jan. 10, 2014, issued by the Japanese Patent Office in corresponding Japanese Patent Application No. 2011-543772, and English language translation of Office Action. (6 pages).

(Continued)

*Primary Examiner* — Gordon J Stock, Jr.
(74) *Attorney, Agent, or Firm* — Buchanan Ingersoll & Rooney PC

(57) ABSTRACT

An apparatus for detecting the position of application of a sealing strip of heat-seal plastic material onto a multilayer web of packaging material for food products advanced along a predetermined path and including at least one base layer for stiffness and strength and one or more heat-seal plastic layers; the sealing strip has a first longitudinal portion, applied onto a longitudinal edge of the web, and a second longitudinal portion projecting laterally from the longitudinal edge. The apparatus comprises a light source for irradiating a transversal portion of the web during movement thereof along its path, and a sensor detecting a quantity related to different behavior of the materials forming the web and the sealing strip to light exposure and generating an output signal related to the width of the second portion of the sealing strip in a direction orthogonal to the web travelling direction and parallel to said web.

16 Claims, 7 Drawing Sheets

(51) Int. Cl.
*G01B 11/02* (2006.01)
*G01B 11/04* (2006.01)
*B29C 65/50* (2006.01)
*B29C 65/78* (2006.01)
*B29C 65/00* (2006.01)
*B29C 65/48* (2006.01)
*B65B 9/20* (2012.01)
*B65B 41/18* (2006.01)
*B29C 53/48* (2006.01)
*B29K 23/00* (2006.01)
*B29K 305/02* (2006.01)
*B29L 9/00* (2006.01)

(52) U.S. Cl.
CPC ......... *B29C65/5092* (2013.01); *B29C 65/7832* (2013.01); *B29C 66/1122* (2013.01); *B29C 66/43* (2013.01); *B29C 66/4312* (2013.01); *B29C 66/4322* (2013.01); *B29C 66/4722* (2013.01); *B29C 66/61* (2013.01); *B29C 66/723* (2013.01); *B29C 66/83413* (2013.01); *B29C 66/84121* (2013.01); *B65B 9/20* (2013.01); *B65B 9/2021* (2013.01); *B65B 41/18* (2013.01); *G01B 11/02* (2013.01); *G01B 11/028* (2013.01); *G01B 11/046* (2013.01); *G01N 21/89* (2013.01); *B29C 53/48* (2013.01); *B29C 66/849* (2013.01); *B29K 2023/06* (2013.01); *B29K 2023/086* (2013.01); *B29K 2305/02* (2013.01); *B29K 2995/0055* (2013.01); *B29K 2995/0067* (2013.01); *B29L 2009/003* (2013.01)

(56) References Cited

U.S. PATENT DOCUMENTS

| | | | | | |
|---|---|---|---|---|---|
| 4,788,442 | A | * | 11/1988 | Sabater et al. | 250/559.36 |
| 4,901,292 | A | * | 2/1990 | Schrauwen | 367/118 |
| 5,724,150 | A | | 3/1998 | Schaede et al. | |
| 6,035,604 | A | | 3/2000 | Gustafsson | |
| 6,460,748 | B1 | * | 10/2002 | Boschi | 226/20 |
| 7,773,226 | B2 | * | 8/2010 | Hofeldt et al. | 356/431 |
| 7,784,247 | B2 | * | 8/2010 | Konno | 53/415 |
| 8,553,228 | B2 | * | 10/2013 | Wilhelm | 356/431 |
| 2003/0133133 | A1 | | 7/2003 | Fujiwara et al. | |
| 2006/0021298 | A1 | | 2/2006 | Van Caeneghem et al. | |
| 2006/0164645 | A1 | * | 7/2006 | Hietanen et al. | 356/430 |
| 2006/0289280 | A1 | | 12/2006 | Furuya et al. | |
| 2009/0293428 | A1 | | 12/2009 | Konno | |

FOREIGN PATENT DOCUMENTS

| | | | |
|---|---|---|---|
| EA | 007256 | B1 | 8/2006 |
| EP | 0 716 287 | A2 | 6/1996 |
| EP | 1967451 | A1 * | 9/2008 |
| JP | 60-162626 | A | 8/1985 |
| JP | 3-167406 | A | 7/1991 |
| JP | 4-54997 | U | 5/1992 |
| JP | 4-295703 | A | 10/1992 |
| JP | 9-5020 | A | 1/1997 |
| JP | 2684460 | B2 | 12/1997 |
| JP | 2006-282372 | A | 10/2006 |
| JP | 2006-343629 | A | 12/2006 |
| JP | 2007-168873 | A | 7/2007 |
| JP | 2008-143561 | A | 6/2008 |
| RU | 2 141 915 | C1 | 11/1999 |
| WO | WO 89/09730 | A1 | 10/1989 |
| WO | WO 00/47947 | A1 | 8/2000 |

OTHER PUBLICATIONS

Office Action issued Sep. 20, 2013, in the Russian Patent Office in corresponding Russian Patent Application No. 2011124871, and an English Translation of the Office Action. (7 pages).
* International Search Report (PCT/ISA/210) issued on Feb. 18, 2010, by European Patent Office as the International Searching Authority for International Application No. PCT/EP2009/065341.
* Written Opinion (PCT/ISA/237) issued on Feb. 18, 2010, by European Patent Office as the International Searching Authority for International Application No. PCT/EP2009/065341.
Mexican Office Action dated Jun. 6, 2013, issued by the Mexican Law of Industrial Property in corresponding Mexican Patent Application No. MX/a/2011/004571 and an English Translation thereof of the Office Action.

* cited by examiner

APPARATUS AND METHOD FOR DETECTING THE POSITION OF APPLICATION OF A SEALING STRIP ONTO A WEB OF PACKAGING MATERIAL FOR FOOD PRODUCTS

TECHNICAL FIELD

The present invention relates to an apparatus and method for detecting the position of application of a sealing strip onto a web of packaging material for food products.

BACKGROUND ART

As it is known, many food products, such as fruit juice, pasteurized or UHT (ultra-high-temperature treated) milk, wine, tomato sauce, etc., are sold in packages made of sterilized packaging material.

A typical example of this type of package is the parallelepiped-shaped package for liquid or pourable food products known as Tetra Brik Aseptic (registered trademark), which is made by folding and sealing a laminated web of packaging material.

The packaging material has a multilayer structure substantially comprising:

- a base layer for stiffness and strength, which may be defined by a layer of fibrous material, e.g. paper, or mineral-filled polypropylene material; and
- a number of layers of heat-seal plastic material, e.g. polyethylene film, covering both sides of the base layer.

In the case of aseptic packages for long-storage products, such as UHT milk, the packaging material also comprises a layer of gas- and light-barrier material, e.g. aluminium foil or ethyl vinyl alcohol (EVOH) film, which is superimposed on a layer of heat-seal plastic material, and is in turn covered with another layer of heat-seal plastic material forming the inner face of the package eventually contacting the food product.

As is known, packages of this sort are produced on fully automatic packaging machines, on which a tube is formed continuously from the web-fed packaging material. More specifically, the web of packaging material is unwound off a reel and fed through an aseptic chamber on the packaging machine, where it is sterilized, e.g. by applying a sterilizing agent such as hydrogen peroxide, which is subsequently evaporated by heating, and/or by subjecting the packaging material to radiation of appropriate wavelength and intensity. The web of packaging material so sterilized is then maintained in a sterile-air environment, and is vertically fed through a number of forming assemblies which interact with the packaging material to fold it gradually from web form into a tube shape.

Afterwards, the tube is filled with the sterilized or sterile-processed food product and is sealed and cut at equally spaced cross sections into pillow-pack packages, which are subsequently folded mechanically to form parallelepiped packages.

Before reaching the forming assemblies, the web of packaging material is fed through an apparatus for applying a sealing strip of heat-seal plastic material, to which the packaging material is subsequently heat sealed to form the vertical tube.

More specifically, the sealing strip is normally heat sealed to the inner plastic layer of the web of packaging material at a pressing station to which the web of packaging material and the sealing strip, both heated beforehand, are fed along different paths, and where the sealing strip is pressed onto a first longitudinal edge of the web of packaging material. After the application, the sealing strip has a first portion heat sealed to the first longitudinal edge of the web, and a second portion projecting therefrom.

On interacting with the forming assemblies, the second longitudinal edge of the web is laid on the outside of the first longitudinal edge with respect to the axis of the tube being formed. More specifically, the sealing strip is located entirely inside the tube, and the face of the second longitudinal edge facing the axis of the tube is superimposed partly on the second portion of the sealing strip, and partly on the face of the first longitudinal edge located on the opposite side to the first portion of the sealing strip.

Apparatus of the above type are known in which the first and second longitudinal edge are heat sealed to form a longitudinal seal along the tube; more specifically, the heat-seal operation comprises a heating step to heat the second longitudinal edge without the sealing strip, and a pressure step to compress the sealing strip and the longitudinal edges.

The heating step melts the polyethylene layer of the second longitudinal edge, which transmits heat by conduction to the first longitudinal edge and the sealing strip, so as to melt the polyethylene layer of the first longitudinal edge and the heat-seal material of the sealing strip.

At the pressure step, the sealing strip and the longitudinal edges of the web of packaging material are pressed together, so that the heat-seal material of the sealing strip and the polyethylene layers of the longitudinal edges blend completely and form the molecular bonds defining the longitudinal seal of the tube.

The sealing strip performs the following functions:
- to prevent the edges of the packaging material forming the longitudinal seal to absorb the packed product;
- to improve the gas barrier properties of the longitudinal seal area;
- to strengthen the longitudinal seal.

In order to properly work, the sealing strip should be correctly positioned with respect to the packaging material.

A need is therefore felt within the industry to control continuously and accurately the position of application of the sealing strip onto the web of packaging material without disturbing the functioning of the packaging machine.

A need is also felt within the industry to adjust the above-mentioned position when necessary, without stopping the packaging machine, to ensure correct application of the sealing strip onto the web of packaging material.

DISCLOSURE OF INVENTION

It is an object of the present invention to provide an apparatus for detecting the position of application of a sealing strip onto a web of packaging material for food products, designed to achieve at least one of the above aims in a straightforward, low-cost manner.

According to the present invention, there is provided an apparatus, for detecting the position of application of a sealing strip onto a web of packaging material for food products, as claimed in claim 1.

The present invention also relates to a method for detecting the position of application of a sealing strip onto a web of packaging material for food products, as claimed in claim 10.

BRIEF DESCRIPTION OF THE DRAWINGS

Two preferred, non-limiting embodiments of the present invention will be described by way of example with reference to the accompanying drawings, in which.

BEST MODE FOR CARRYING OUT THE INVENTION

Figure 1:
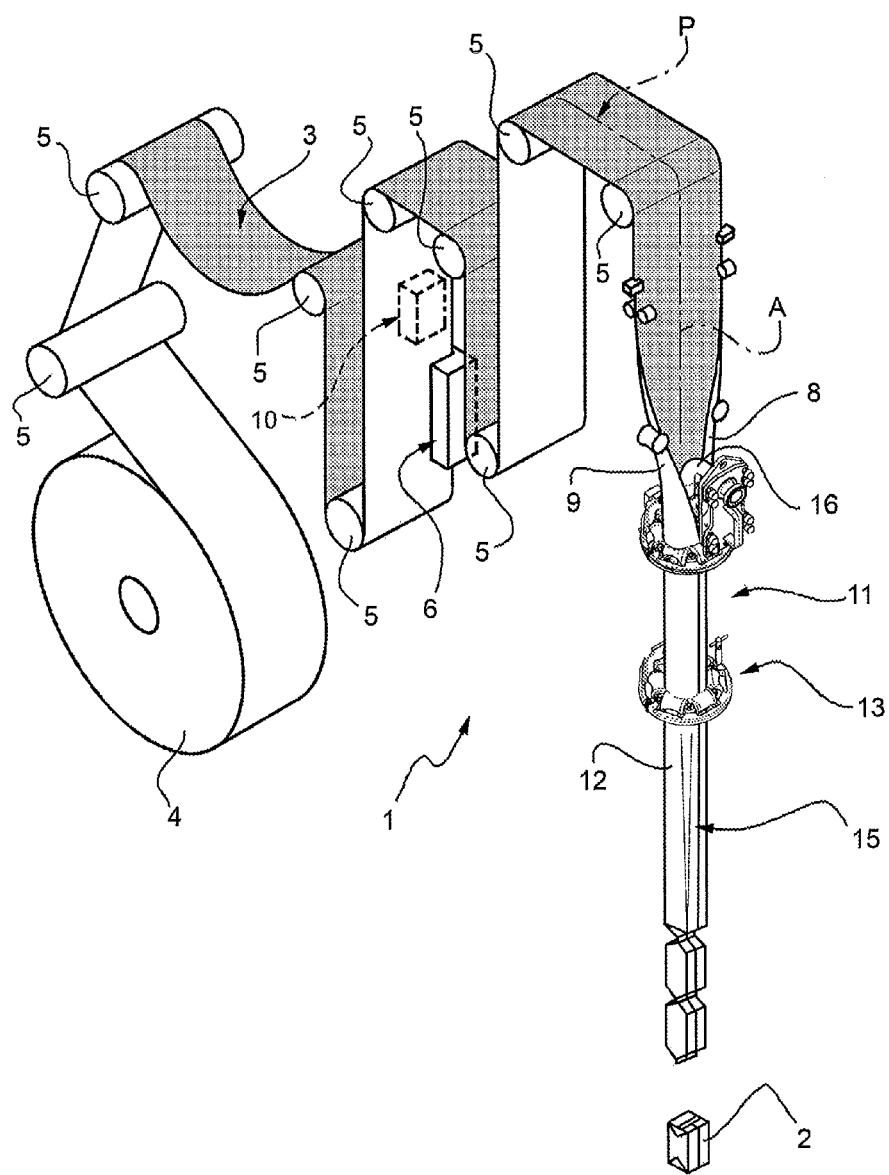
FIG. 1 shows a schematic view in perspective of a packaging machine adapted to produce sealed packages of a food product from a web of packaging material and including an apparatus, in accordance with a first embodiment of the present invention, for detecting the position of application of a sealing strip onto said web.

Number 1 in FIG. 1 indicates as a whole a packaging machine for continuously producing sealed packages 2 of a food product from a web 3 of packaging material, which is unwound off a reel 4 and fed along a forming path P.

Machine 1 preferably produces sealed packages 2 of a pourable food product, such as pasteurized or UHT milk, fruit juice, wine, etc.

Machine 1 may also produce sealed packages 2 of a food product that is pourable when producing packages 2, and sets after packages 2 are sealed. One example of such a food product is a portion of cheese, that is melted when producing packages 2, and sets after packages 2 are sealed.

The packaging material has a multilayer structure substantially comprising:
 a base layer for stiffness and strength, which may be defined by a layer of fibrous material, e.g. paper, or mineral-filled polypropylene material; and
 a number of layers of heat-seal plastic material, e.g. polyethylene film, covering both sides of the base layer.

In the case of aseptic packages for long-storage products, such as UHT milk, the packaging material also comprises a layer of gas- and light-barrier material, e.g. preferably an aluminum foil or even an ethyl vinyl alcohol (EVOH) film, which is superimposed on a layer of heat-seal plastic material, and is in turn covered with one or more layers of heat-seal plastic material forming the inner face of the package eventually contacting the food product.

As shown in FIG. 1, web 3 is fed along path P by guide members 5, e.g. rollers or similar, and successively through a number of work stations or apparatus, of which FIG. 1 shows schematically: an apparatus 6 for applying a sealing strip 7 of heat-seal plastic material (shown in FIGS. 2 to 5 and 7 to 8) to one (8) of the opposite longitudinal edges 8, 9 of web 3; an apparatus 10 in accordance with the present invention for detecting the position of application of sealing strip 7 onto web 3; a forming apparatus 11 for forming a tube 12 of packaging material by folding web 3 into a cylinder around an axis A so as to superimpose longitudinal edge 9 of web 3 over longitudinal edge 8 and sealing strip 7; and a sealing apparatus 13 for heat sealing longitudinal edges 8, 9 and sealing strip 7 so as to form, along tube 12, a longitudinal seal 15 parallel to, and spaced from, axis A.

As it is commonly known, machine 1 also comprises a filling apparatus 16, for pouring the sterilized or sterile-processed food product continuously into tube 12 of packaging material, and a jaw-type forming apparatus (not shown) for gripping, sealing, and cutting tube 12 along equally spaced cross sections to form a succession of packages 2.

Figure 2:
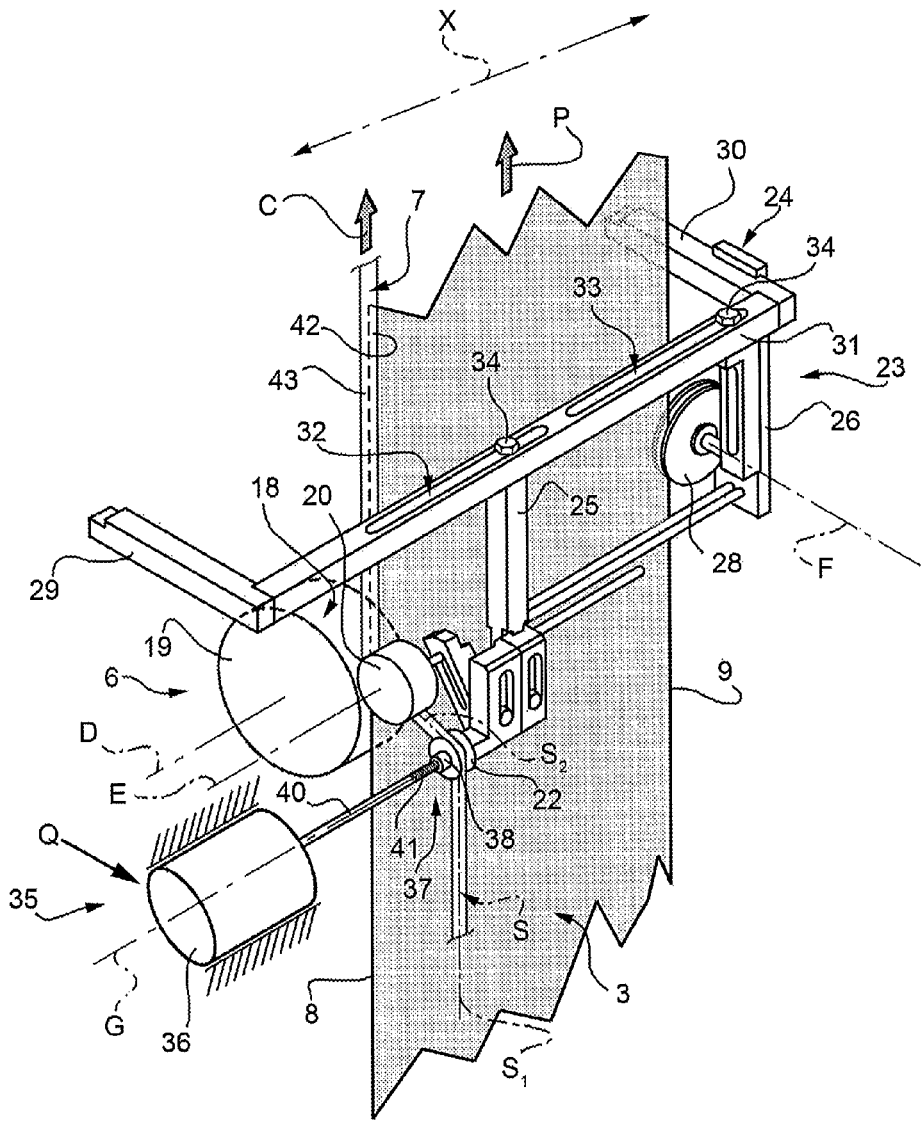
FIG. 2 shows a larger-scale view in perspective of a sealing unit of the FIG. 1 machine for sealing the sealing strip onto the web of packaging material.

With particular reference to FIG. 2, sealing strip 7 is fed to applying apparatus 6 along a path S having a straight portion C in common with path P of web 3, along which sealing strip 7 is heat sealed under pressure to longitudinal edge 8 of the plastic layer of web 3 forming the inner face of packages 2 eventually contacting the food product.

More specifically, path S comprises, in addition to portion C in common with path P, a straight upstream portion $S_1$ parallel to the adjacent portion of path P, and an oblique portion $S_2$ connecting portion $S_1$ to portion C.

Applying apparatus 6 comprises a pressing device 18 for pressing sealing strip 7 onto web 3 and defining the common portion C of paths P and S, and a heat-treating device (known per se and not shown) for preheating sealing strip 7 and web 3 along respective paths S and P upstream from pressing device 18.

Pressing device 18 comprises a pair of pressure rollers 19, 20 having respective parallel axes D, E, rotating in opposite directions, and located adjacent to each other to define a small-section passage through which sealing strip 7 and the portion of web 3 containing longitudinal edge 8 are rolled simultaneously. In particular, axes D, E are parallel to web 3 and orthogonal to portion C of paths P, S and to the travelling direction of web 3 and sealing strip 7 through rollers 19, 20.

In the zone of pressing device 18, opposite longitudinal edge 9 of web 3 cooperates with a guide roller 28 having an axis F orthogonal to axes D, E and to portion C of paths P, S.

In the preferred embodiment, one (19) of pressure rollers 19, 20 is much larger in diameter than the other (20) though it should be noted that rollers having the same diameter may also be used.

In the example shown, sealing strip 7 extends about the smaller-diameter pressure roller 20, and about a guide roller 22 having an axis G parallel to axes D, E of rollers 19, 20, and located at the junction of portions $S_1$ and $S_2$ of path S.

Rollers 20, 22 and 28 are both mounted on a supporting structure 23 which allows to adjust:
 the distance along a direction X parallel to axes D, E, G between roller 28, on the one hand, and rollers 20, 22, on the other hand, as a function of the width of the web 3 processed; and
 the position of roller 22, and therefore the position of the sealing strip 7, with respect to web 3 along direction X.

In particular, supporting structure 23 includes a C-shaped horizontal frame 24 attached to the machine frame (not shown), and a pair of vertical braces 25, 26 suspended from frame 24; one (25) of the vertical braces 25, 26 carries rollers 20, 22, whilst the other (26) carries guide roller 28.

More precisely, frame 24 includes a pair of side bars 29, 30, parallel to axis F, and a cross member 31 parallel to axes D, E, G and connected to respective frontal ends of side bars 29, 30 so as to be located in use in a position facing the side of web 3 designed to form the inner face of packages 2.

Both braces 25, 26 have their upper ends slidably coupled to respective slots 32, 33 provided along cross member 31 and elongated parallel to direction X and axes D, E, G. In this way, the position of rollers 20, 22, 28 may be manually adjusted before starting production of packages 2 so as to adapt the distance between braces 25, 26 to the width of the web 3 processed. A similar adjustment is also done for roller 19 in an analogous way not shown. When the positions of the upper ends of braces 25, 26 along respective slots 32, 33 have been determined, braces 25, 26 are locked in those positions to cross member 31 by tightening respective nuts 34.

Roller 22 is smaller in axial length than roller 20 and actuator means 35 are provided for adjusting position of roller 22, and therefore sealing strip 7, along direction X with respect to roller 20 and web 3; the displacement of roller 22 along direction X is necessarily limited by the axial length of roller 20 so that the latter may feed sealing strip 7 to the application zone onto web 3.

Actuator means 35 comprises an electric motor 36 and a screw assembly 37 interposed between motor 36 and roller 22.

In particular, assembly 37 includes a nut screw 38 provided on the radially inner portion of roller 22 and a screw element 40 coupled to nut screw 38 and to an output shaft (not shown) of motor 36. More specifically, screw element 40 has one end coupled to a bottom end of brace 25, an opposite end angularly coupled to the output shaft of motor 36 and an intermediate threaded portion 41 engaging a corresponding thread of nut screw 38. Due to the links to motor 36 and brace 25, any axial displacement of screw element 40 is prevented; therefore, rotation of screw element 40 around its axis necessarily produces a displacement of nut screw 38, and therefore roller 22, along direction X, with a consequent movement of sealing strip 7 along the same direction with respect to web 3.

As a result of the position adjustments of rollers 19, 20, 22 and 28, only a first longitudinal portion 42 of sealing strip 7 is applied by pressing device 18 onto longitudinal edge 8 of web 3, while a further longitudinal portion 43 of strip 7 projects from edge 8, so that it will be eventually applied onto the opposite edge 9 of web 3 when tube 12 will be formed.

As previously mentioned, in its final position inside packages 2, sealing strip 7 prevents edge 8 from absorbing the food product once tube 12 and longitudinal seal 15 are formed, and also provides for improving the gas-barrier performance and physical strength of seal 15.

With reference to FIGS. 1 and 3 to 5, detecting apparatus 10 is located downstream from pressing device 18 along path P and essentially comprises a light source 45, configured for irradiating a transversal portion of continuously moving web 3, and a sensor 46 in use detecting a quantity related to the different behavior of the materials forming web 3 and sealing strip 7 to light exposure and generating an output signal W related to the width of longitudinal portion 43 of sealing strip 7 in direction X.

Figure 3:
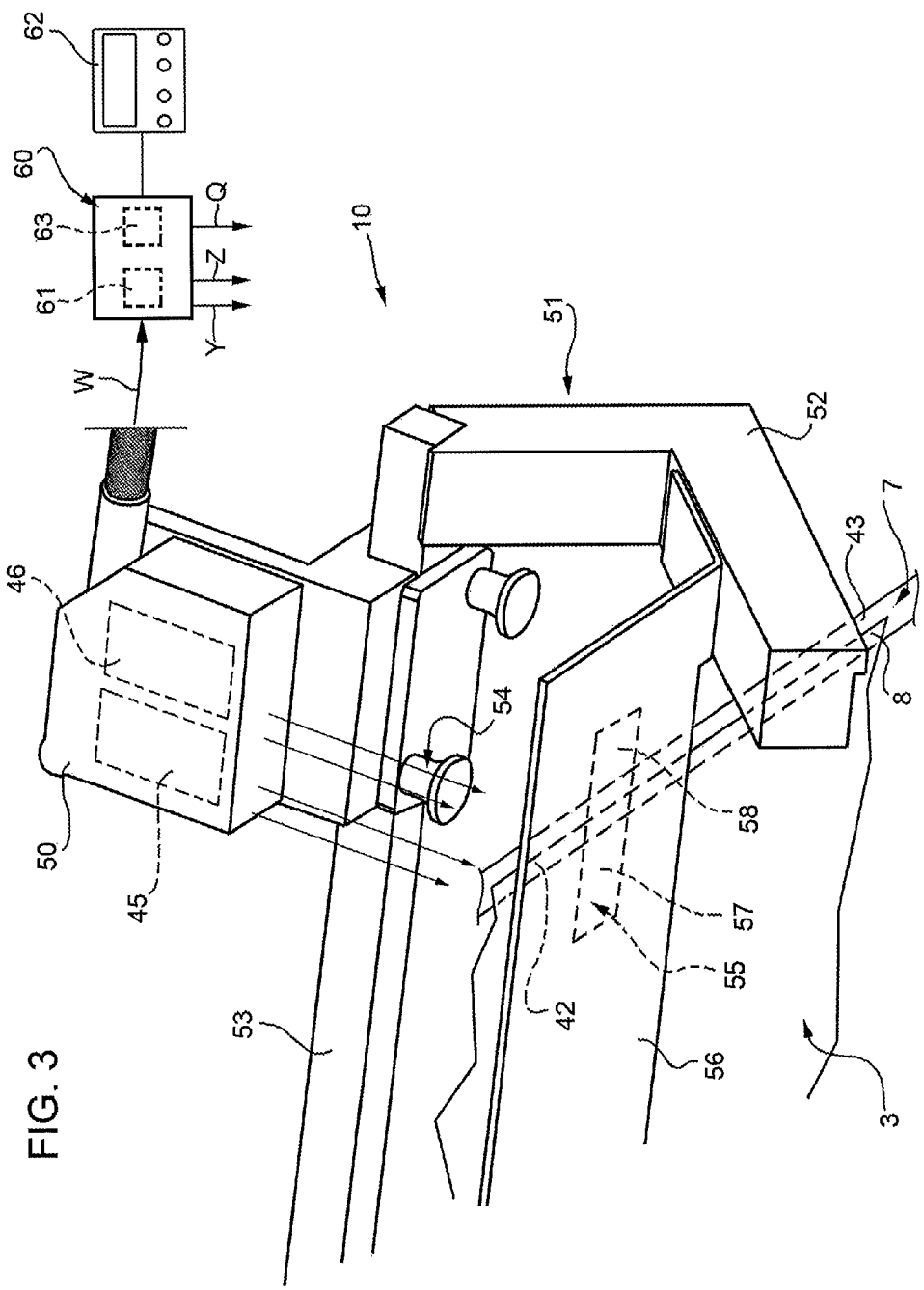
FIG. 3 shows a first larger-scale view in perspective of the FIG. 1 detecting apparatus.
Figure 4:
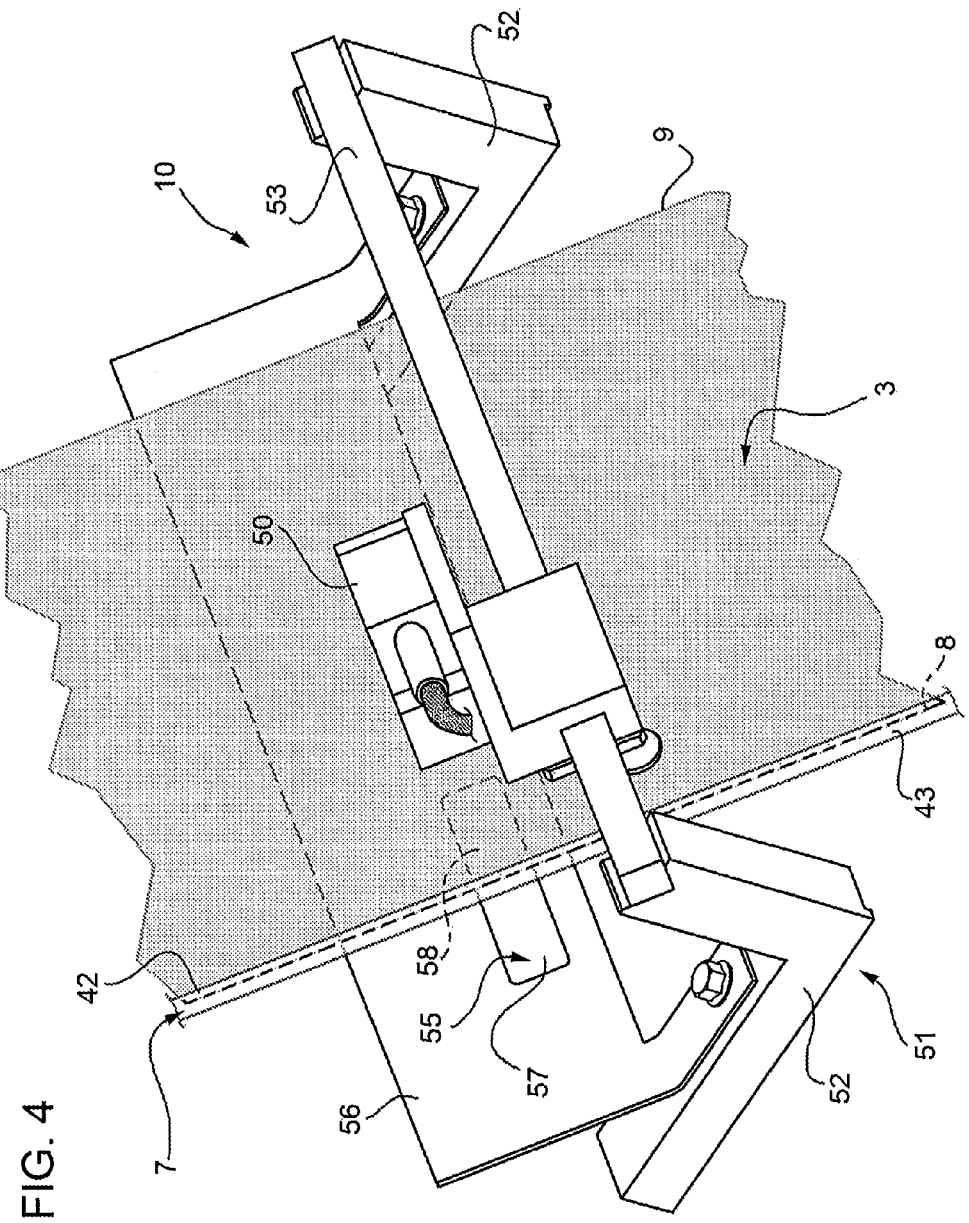
FIG. 4 shows a second view in perspective of the FIG. 3 detecting apparatus.
Figure 5:
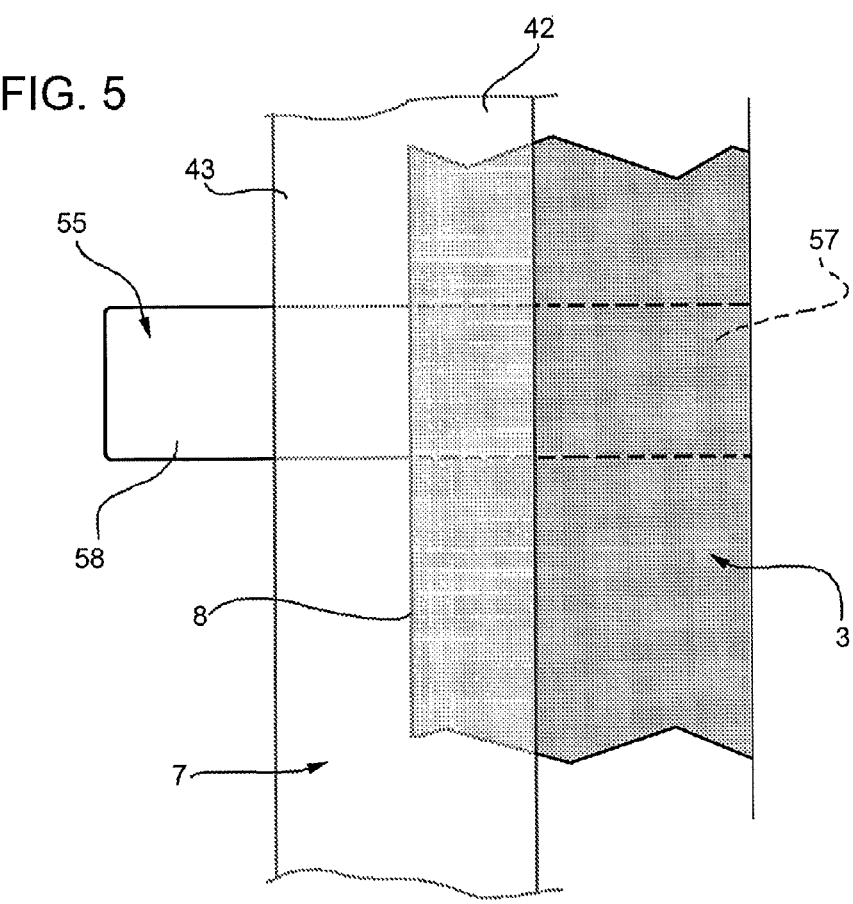
FIG. 5 shows a larger-scale top plan view of the web material after the application of the sealing strip and during the passage through the detecting apparatus of FIGS. 3 and 4.

In the embodiment shown in FIGS. 3 to 5, light source 45 and sensor 46 are both arranged on the same side of web 3 and are preferably incorporated in a single box 50; in this case, the quantity detected by sensor 46 is the intensity I of the light reflected by the irradiated materials.

In particular, box 50 is mounted on a supporting frame 51 attached in a conventional manner to the machine frame (not shown). More specifically, supporting frame 51 includes a pair of lateral L-shaped brackets 52, in use arranged at the opposite sides of web 3, and a cross bar 53 connecting the upper ends of brackets 52, extending along direction X and carrying box 50.

As shown in FIGS. 3 and 4, bar 53 and box 50 face the side of web 3 which is designed to eventually define the inner surface of packages 2 and on which sealing strip 7 is applied.

Box 50 is slidably coupled to bar 53 so that its position along direction X can be adjusted; conventional fastening means 54 allows locking of box 50 on bar 53 at the desired position.

In order to obtain a better detection result, a reflecting surface 55 is arranged at the opposite side of web 3 to box 50; in particular, reflecting surface 55 preferably has a rectangular shape and is provided on a plate 56 supported by the bottom portions of brackets 52, extending parallel to, and spaced from, web 3 and facing the side thereof eventually defining the outer surface of packages 1

In the position of arrangement on plate 56, reflecting surface 55 has a first portion 57 covered by web 3 and sealing strip 7 with respect to light source 45, and a second portion 58 laterally protruding from longitudinal portion 43 of strip 7 and facing light source 45.

The size of reflecting surface 55 in direction X is chosen to allow detection of sealing strip 7 on webs 3 having different widths.

Figure 6:
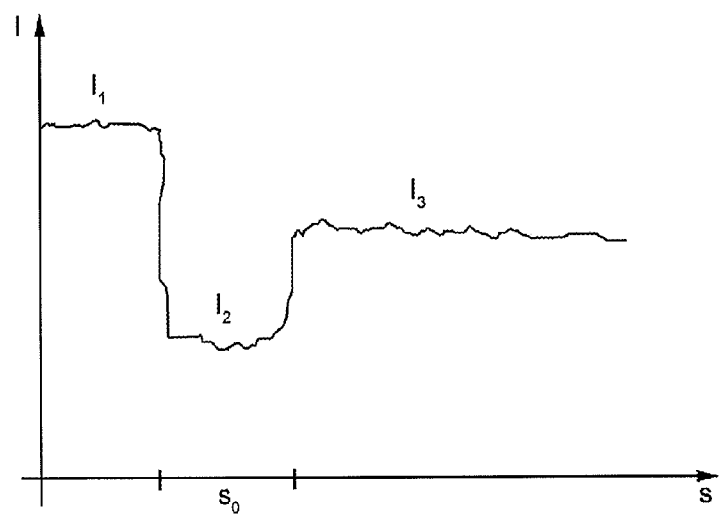
FIG. 6 shows a graph illustrating the variations of a characteristic quantity measured by the detecting apparatus of FIGS. 3 and 4 at and around the zone of application of the sealing strip onto the web of packaging material.

As shown in FIG. 6, the intensity I of reflected light as detected by sensor 46 along a transversal band of web 3 (in the graph, space s) reaches the highest values $I_1$ at portion 58 of reflecting surface 55, which is not covered by other materials, the lowest values $I_2$ at longitudinal portion 43 of sealing strip 7, which covers reflecting surface 55 at a distance thereof and is constituted by an opaque material, and intermediate values $I_3$ at the remaining irradiated region of web 3, which is in part covered by longitudinal portion 42 of sealing strip 7 lying thereupon with no practical effect on the reflected light.

Values $I_2$ in the graph of FIG. 6 allow to identify the width $s_0$ of longitudinal portion 43 of sealing strip 7 along direction X and, therefore, the position of both portions 42, 43 of sealing strip 7 with respect to web 3.

Output signal W, generated by sensor 46 on the basis of the reflected light detected during operation of machine 1, is a current signal, which is proportional to the width of longitudinal portion 43 of sealing strip 7.

An electronic processing unit 60 receives output signal W and includes converting means 61 for converting the current values into strip width values shown on an operator display 62, and control means 63 for generating the following control signals:

an alarm signal Y when the detected width of longitudinal portion 43 of strip 7 is out of a predetermined range R of acceptable values, i.e. it is smaller than a first threshold value $R_1$ or larger than a second threshold value $R_2$; and a machine stop signal Z when the detected width of longitudinal portion 43 of strip 7 is out of range R for a time period greater than a threshold time interval T.

An example of a situation in which the detected width of longitudinal portion 43 of sealing strip 7 is smaller than threshold value $R_1$ is when sealing strip 7 is applied with a too large portion (42) on edge 8 of web 3; in a completely analogous manner, an example of a situation in which the detected width of longitudinal portion 43 of sealing strip 7 is larger than threshold value $R_2$ is when sealing strip 7 is applied with a too small portion (42) on edge 8 of web 3.

The control signals generated by processing unit 60 may also include a further signal Q for driving motor 36 in order to adjust the position of roller 22, and therefore of sealing strip 7, with respect to web 3 along direction X; signal Q may be used in combination with signals Y, Z.

In actual use, web 3 is unwound off reel 4 and fed along path P in the direction shown in FIG. 1.

More specifically, web 3 is fed by guide members 5 along path P and through successive apparatus 6, 10, 11 and 13.

At apparatus 6, after a pre-heating of the materials to seal, longitudinal portion 42 of sealing strip 7 is applied under pressure to the face of edge 8 of web 3 eventually facing inwards of packages 2. This step is performed by pressing rollers 19, 20. Once longitudinal portion 42 of sealing strip 7 is applied to edge 8 of web 3, longitudinal portion 43 projects from that edge.

In a position immediately close to pressing device 18, apparatus 10 continuously detects the position of sealing strip 7 on web 3. In particular, a transversal portion of web 3 is continuously irradiated by a light beam generated by light source 45. The light beam is then reflected with different intensities depending on the irradiated materials: in particular, as previously mentioned and clearly shown in FIG. 6, the intensity I of reflected light as detected by sensor 46 reaches the maximum values $I_1$ at portion 58 of reflecting surface 55, the minimum values $I_2$ at longitudinal portion 43 of sealing strip 7, which is spaced from reflecting surface 55, and intermediate values $I_3$ at the remaining irradiated region of web 3, which is partly attached to longitudinal portion 42 of sealing strip 7.

In this way, it is possible to determine the width of the longitudinal portion (43) of sealing strip 7 which is not attached to web 3. Sensor 46 generates an output signal W which is proportional to the detected strip width.

When this width is out of range R, processing unit 60 generates alarm signal Y; packages 2 formed during this stage are then wasted at the end of the cycle.

If the detected strip is out of range R for a time period greater than threshold time interval T, processing unit 60 generates machine stop signal Z.

Processing unit 60 may also generate control signal Q for activating motor 36 to modify the position of roller 22, and therefore of sealing strip 7, with respect to web 3 along direction X; in this case, signals Y and Z are only generated when the correction of the position of sealing strip 7 cannot be performed.

In particular, when signal Q is generated, motor 36 produces the rotation of screw element 40 around its axis without any axial displacement; consequently, nut screw 38 is axially moved along threaded portion 41 of screw element 40 and modifies the position of roller 22 along direction X up to the width of longitudinal portion 43 of sealing strip 7 as detected by sensor 46 gets back within range R.

Next, web 3 passes through forming apparatus 11, wherein it is gradually folded into a cylinder around axis A so as to superimpose longitudinal edge 9 over longitudinal edge 8 and sealing strip 7 and form tube 12 not yet sealed longitudinally; in particular, sealing strip 7 is located inside the as yet unsealed tube 12, edge 9 is located radially outwards of edge 8 and longitudinal portion 43 of sealing strip 7 with respect to axis A, and edge 8 is located radially outwards of longitudinal portion 42 of strip 7.

At sealing apparatus 13, edge 9 of web 3 is heated to melt the polyethylene layer, and heat is transmitted by conduction from edge 9 to edge 8 and sealing strip 7 to melt the polyethylene layer of edge 8 and the heat-seal material of strip 7. In this way, longitudinal seal 15 is formed.

After this step, the sterilized or sterile-processed food product is continuously poured into tube 12, which is in turn gripped, sealed and cut along equally spaced cross sections to form a succession of packages 2.

Figure 7:
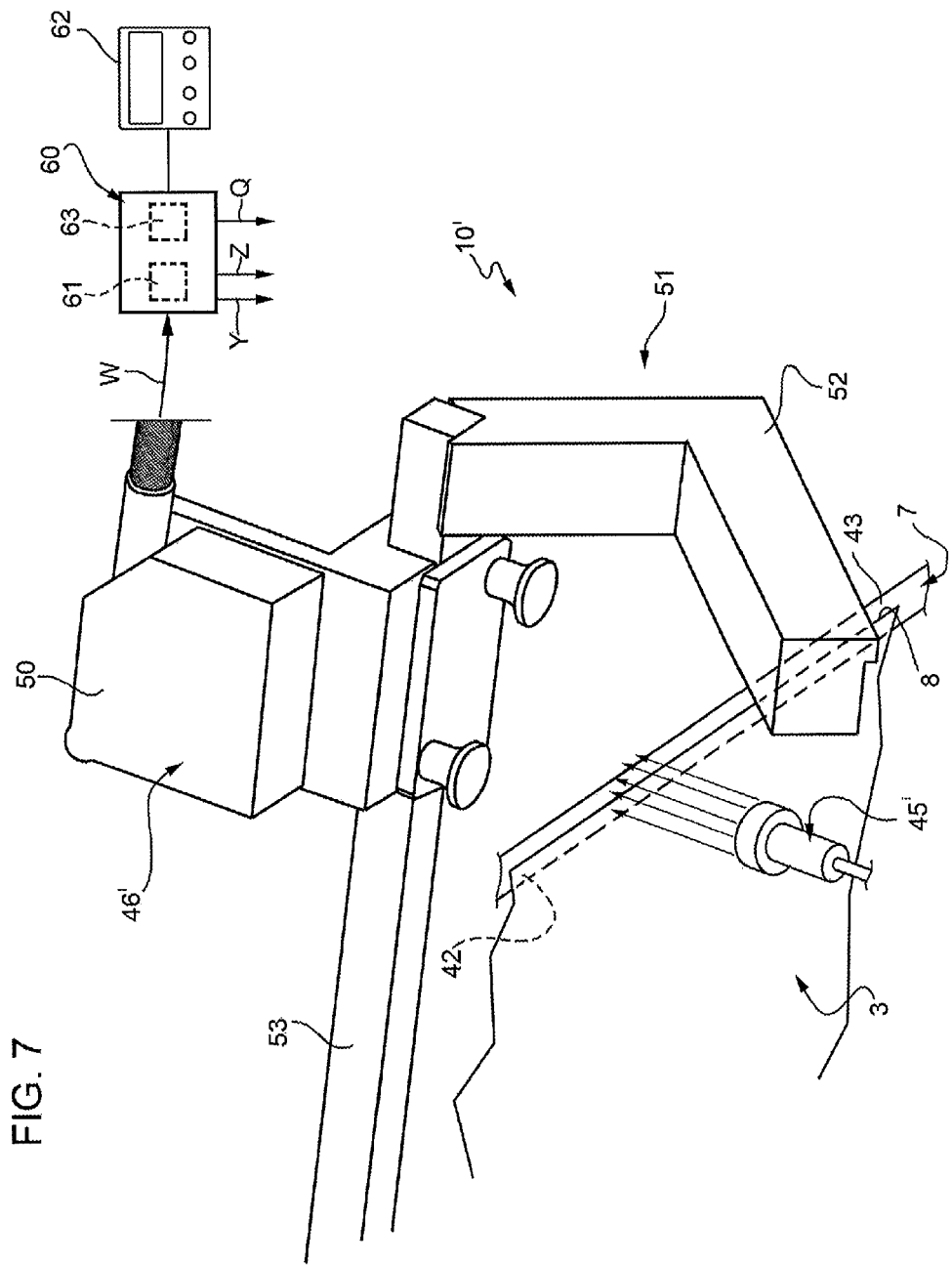
FIG. 7 shows a larger-scale view in perspective of a detecting apparatus in accordance with a different embodiment of the present invention.
Figure 8:
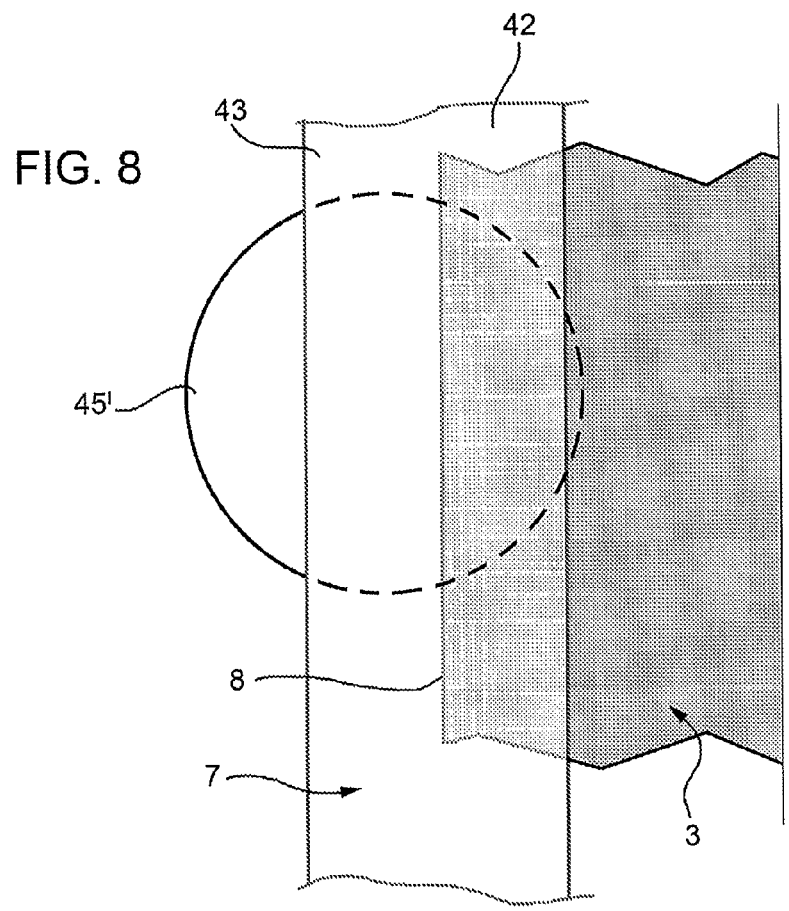
FIG. 8 shows a larger-scale top plan view of the web material after the application of the sealing strip and during the passage through the FIG. 7 detecting apparatus.

Number 10' in FIGS. 7 and 8 indicates a detecting apparatus in accordance with a different embodiment of the present invention.

Detecting apparatus 10' being similar to apparatus 10, the following description is limited to the differences between the two, and using the same reference numbers, where possible, for identical or corresponding parts of apparatus 10 and 10'.

In particular, apparatus 10' differs from apparatus 10 by light source 45' and sensor 46' being arranged at opposite sides of web 3. In this case, the quantity detected by sensor 46' is the intensity I' of the direct light passing through the different materials of sealing strip 7 and web 3.

More specifically, sensor 46' is arranged on supporting frame 51 in the same manner as box 50, while light source 45' irradiates the side of web 3 eventually defining the outer surface of packages 2.

This embodiment is particularly recommended for the packaging material for chilled products, wherein the barrier layer is absent and the base layer is made up of a brown-coloured paper, which may impair the right working of the solution based on detection of reflected light.

Figure 9:
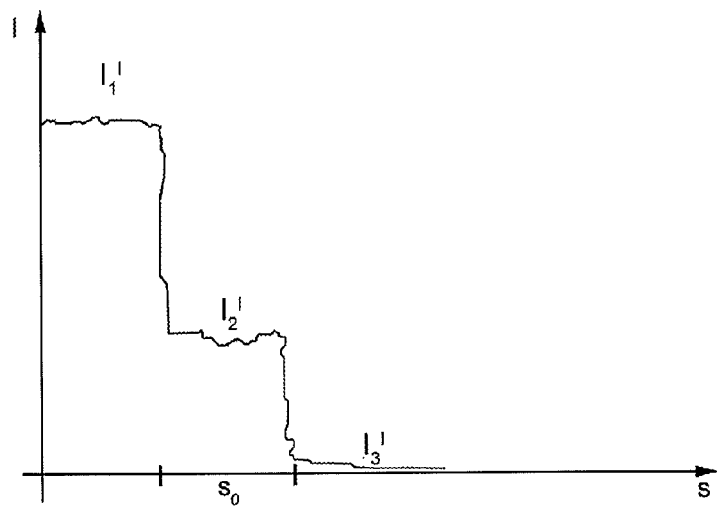
FIG. 9 shows a graph illustrating the variations of a characteristic quantity measured by the FIG. 7 detecting apparatus at and around the zone of application of the sealing strip onto the web of packaging material.

As shown in FIG. 9, the intensity I' of direct light as detected by sensor 46' reaches the highest values $I_1$' on the outside of web 3 and sealing strip 7, where sensor 46' is directly irradiated by light source 45', the lowest values $I_3$' at the irradiated region of web 3, with or without sealing strip 7, where practically light does not pass at all, and intermediate values $I_2$' at longitudinal portion 43 of sealing strip 7.

Operationwise, detecting apparatus 10' differs from detecting apparatus 10 only in the way the width of longitudinal portion 43 of sealing strip 7 is detected, i.e. through a direct light instead of a reflected light.

The advantages of detecting apparatus 10, 10' and the detecting method according to the present invention will be clear from the above description.

In particular, detecting apparatus 10, 10' allow to control continuously and accurately the position of application of sealing strip 7 onto web 3 of packaging material without disturbing the functioning of packaging machine 1. The detecting operation is very simple and does not require elaborate calculations or interpolations to determine whether the sealing strip is or is not correctly applied on web 3. In fact, the measure of the width of the longitudinal portion (43) of sealing strip 7 protruding from web 3 directly gives the information about the correctness of the application of the sealing strip.

Moreover, the output signal W coming from sensor 46, 46' may also be used as a feedback to control and not only to monitor the position of strip 7 on web 3.

Clearly, changes may be made to detecting apparatus 10, 10' and the detecting method as described herein without, however, departing from the scope of protection of the accompanying claims.

The invention claimed is:

1. An apparatus for detecting a position of application of a sealing strip of heat-seal plastic material onto a multilayer web of packaging material for food products advanced along a predetermined path in a travelling direction and including at least one base layer for stiffness and strength and one or more heat-seal plastic layers, said sealing strip having a first longitudinal portion, applied onto a longitudinal edge of said web, and a second longitudinal portion projecting laterally from said longitudinal edge, said apparatus comprising:

a light source configured for irradiating a transversal portion of said web during movement of the web along said path; and a sensor in use detecting a quantity related to different behavior of materials forming the web and the sealing strip to light exposure and generating an output signal related to a width of said second longitudinal portion of said sealing strip in a direction orthogonal to the travelling direction of the web and parallel to said web.

2. An apparatus as claimed in claim 1, wherein said light source and said sensor are arranged at opposite sides of said web and wherein the quantity detected by the sensor is an intensity of direct light passing through different materials of the sealing strip and the web.

3. An apparatus as claimed in claim 1, further comprising an electronic processing unit that includes a part receiving said output signal from said sensor and generating an alarm signal when a detected width of the second portion of the sealing strip is out of a predetermined range of acceptable values, and/or a control signal for controlling a position of feeding means of said sealing strip with respect to said web.

4. An apparatus as claimed in claim 1, wherein said light source and said sensor are arranged at a common side of said web, and wherein the quantity detected by said sensor is an intensity of light reflected by irradiated materials.

5. An apparatus as claimed in claim 2, wherein detected values of the intensity of the light corresponding to the second longitudinal portion of the sealing strip are different from detected values corresponding to both sides of said second longitudinal portion.

6. An apparatus as claimed in claim 3, wherein said part of the electronic processing unit generates a stop signal when the detected width of the longitudinal portion of the sealing strip is out of said range for a time period greater than a threshold time interval.

7. An apparatus as claimed in claim 4, further comprising a reflecting surface arranged at a side of said web opposite to said sensor and said light source, the reflecting surface having a first portion, covered by the web and the sealing strip with respect to the light source, and a second portion laterally protruding from the second longitudinal portion of said sealing strip and facing said light source.

8. An apparatus as claimed in claim 7, wherein said second portion of said sealing strip is spaced from said first portion of said reflecting surface.

9. A packaging machine for producing sealed packages of food product from a web of packaging material, comprising an applying apparatus for applying said sealing strip to said web and a detecting apparatus as claimed in claim 1.

10. A packaging machine as claimed in claim 9, wherein said applying apparatus comprises a sealing device for sealing said sealing strip to said longitudinal edge of said web, feeding means for feeding said sealing strip to said applying apparatus, support means bearing said feeding means in an adjustable position along an adjusting direction orthogonal to the travelling direction of the web, actuator means which can be selectively activated for displacing the feeding means in a desired position with respect to said web along the adjusting direction, and control means receiving said output signal from said sensor and generating a control signal for controlling a position of said feeding means with respect to said web.

11. A method for detecting a position of application of a sealing strip of heat-seal plastic material onto a multilayer web of packaging material for food products advanced along a predetermined path in a travelling direction and including at least one base layer for stiffness and strength and one or more heat-seal plastic layers, said sealing strip having a first longitudinal portion, applied onto a longitudinal edge of said web, and a second longitudinal portion projecting laterally from said longitudinal edge, said method comprising:

generating a light beam on a transversal portion of said web during movement of the web along said path;

detecting a quantity related to different behavior of materials forming the web and the sealing strip to light exposure; and generating an output signal related to a width of said second portion of said sealing strip in a transversal direction orthogonal to the travelling direction of the web and parallel to said web.

12. A method as claimed in claim 11, wherein said light beam is generated from one side of said web, and the detected quantity is an intensity of direct light passing through different materials of the sealing strip and the web and received by a sensor at the opposite side of said web.

13. A method as claimed in claim 11, wherein said generating of the light beam comprises generating the light beam from one side of said web, and the detecting of the quantity comprises detecting an intensity of light reflected by irradiated materials.

14. A method as claimed in claim 11, further comprising generating, on the basis of said output signal:

an alarm signal, when a detected width of the second portion of the sealing strip is out of a determined range of acceptable values; and/or a control signal for controlling a position of said sealing strip with respect to said web along said transversal direction.

15. A method as claimed in claim 13, wherein said light beam is directed on said web, said sealing strip and a reflecting surface having a first portion, covered by the web and the sealing strip, and a second portion laterally protruding from the second portion of said sealing strip.

16. A method as claimed in claim 14, further comprising generating a stop signal when the detected width of the longitudinal portion of the sealing strip is out of said range for a time period greater than a threshold time interval.

* * * * *